US009060850B2

(12) United States Patent
Young (10) Patent No.: US 9,060,850 B2
(45) Date of Patent: Jun. 23, 2015

(54) METHOD AND SYSTEM FOR MAKING AN APPARATUS FOR INDIVIDUALIZED AREA-SPECIFIC SKIN TREATMENTS FOR A SUBJECT

(71) Applicant: Daniel L. Young, Henderson, NV (US)

(72) Inventor: Daniel L. Young, Henderson, NV (US)

(73) Assignee: Forever Young International, Inc., Henderson, NV (US)

( * ) Notice: Subject to any disclaimer, the term of this patent is extended or adjusted under 35 U.S.C. 154(b) by 179 days.

(21) Appl. No.: 13/765,354

(22) Filed: Feb. 12, 2013

(65) Prior Publication Data

US 2013/0152370 A1 Jun. 20, 2013

Related U.S. Application Data

(63) Continuation of application No. 12/321,757, filed on Jan. 23, 2009, now Pat. No. 8,372,130.

(51) Int. Cl.
| | |
|---|---|
| *A61K 8/02* | (2006.01) |
| *A61F 7/02* | (2006.01) |
| *A61F 7/03* | (2006.01) |
| *A61F 7/00* | (2006.01) |

(52) U.S. Cl.
CPC ......... *A61F 7/0241* (2013.01); *Y10T 29/49885* (2015.01); *A61F 7/03* (2013.01); *A61F 2007/0003* (2013.01); *A61F 2007/0258* (2013.01); *A61F 2007/0261* (2013.01)

(58) Field of Classification Search
CPC .............. A61F 7/02; A61F 2007/0002; A61F 2007/0004; A61F 7/007
USPC .......................................... 424/401; 607/109
See application file for complete search history.

(56) References Cited

U.S. PATENT DOCUMENTS

| | | | |
|---|---|---|---|
| 6,974,470 | B2 | 12/2005 | Tsunakawa et al. |
| 2001/0049546 | A1 | 12/2001 | Dvoretzky et al. |
| 2007/0142882 | A1 | 6/2007 | Quincy et al. |
| 2009/0149925 | A1 | 6/2009 | Macdonald et al. |
| 2009/0280150 | A1* | 11/2009 | Kamen et al. ................. 424/401 |

* cited by examiner

*Primary Examiner* — Catherine Voorhees
*Assistant Examiner* — Philip Edwards
(74) *Attorney, Agent, or Firm* — Troutman Sanders, LLP (57) ABSTRACT

A temperature controlled cosmetic treatment facial mask with area-specific treatments of the present invention includes a substantially planar mask body which is formed with cut-outs for a person's eyes, nose, and mouth. The mask may include a number of large and small area treatment zones in combination with asymmetrical treatment zones suitable for treatment of specific and localized skin conditions. The treatments zones are coated with skin treatments, such as compounds, lotions, gels, and the like as are known in the facial treatment, cosmetics, spa and medical industry. The mask may include a self-heating or cooling substrate to provide temperature control to the face mask and each mask may include heating areas, cooling areas, or both. A system is also provided that includes an imaging device that feeds its output to a central computer system having an image analyzer, CPU, memory and Look Up Table, and face map for determining specific treatment requirements for the particular patient. An output from the central computer system is provided to a treatment deposition device which deposits various treatments onto an intermediate membrane layer to generate a custom temperature controlled facial mask with area-specific treatments for that particular patient.

8 Claims, 7 Drawing Sheets

METHOD AND SYSTEM FOR MAKING AN APPARATUS FOR INDIVIDUALIZED AREA-SPECIFIC SKIN TREATMENTS FOR A SUBJECT

CROSS-REFERENCE TO RELATED APPLICATIONS

This application is a Continuation application of U.S. application Ser. No. 12/321,757, entitled "Temperature Controlled Facial Mask with Area-Specific Treatments" and filed Jan. 23, 2009, which is incorporated by reference in its entirety into this application as if set forth verbatim.

FIELD OF THE INVENTION

The present invention relates generally to the cosmetics and spa industry. The present invention is more particularly, though not exclusively, useful as a facial mask having area-specific treatments and the ability to create hot or cold areas on the mask.

BACKGROUND OF THE INVENTION

For centuries, various lotions and creams have been used to treat a variety of skin conditions. This is particularly so in recent years as the facial mask has become a more popular portion of a spa treatment. A facial mask typically consists of the application of a thick cream-like beauty product to the face. Since their introduction, facial masks have become a staple in many women's beauty regimen both at home and in professional spas. Facial masks are particularly popular due to their versatility and their ability to be customized with various skin treatments to meet a variety of skin health and beauty needs for each individual person.

People have used a variety of facial masks for centuries. Some of the early accounts of facial treatments include the use of river clay, mud and fruit being applied to the face for beauty purposes. For instance, people have used Dead Sea mud, known for its high mineral content, as a base material for facial masks for many years. In more modern approaches, facial masks may take traditional facial recipes and couple them with more modern pharmaceutical medications or highly concentrated vitamin extracts.

Facial masks are rarely the only part of a facial treatment. Instead, a facial mask is typically just one specific element in a woman's overall beauty routine. Nevertheless, facial masks can be one of the most important elements for cleaning and purifying facial skin in preparation for subsequent skin treatments. For example, various facial masks are often used to clean and tone facial skin before applying makeup. Facial masks can also be used for health and medical purposes, such as healing burns, post-surgical treatment, and reducing the appearance of scars and other skin blemishes.

Traditional facial masks are usually built on a solution base, including for instance a clay or mud-based suspension. This solution base is often infused and may be mixed with other active or inactive ingredients so that the end product is a thick compound which may have a smooth creamy texture. The various ingredients combined can vary significantly, and are often selected for the known, or sometimes even the perceived, effects these ingredients have on the skin. For instance, users may apply a hydrating and wrinkle-reducing facial mask to the skin surrounding the eyes, nose and mouth. In order for this type of solution to be most effective in its purpose, it must be left on for a specified amount of time. In fact, depending on the contents of the mask, some facial masks are intended to be left on until dry, while other facial masks are intended to be removed after only a few minutes.

In some instances, a facial mask consists of a technician applying a liquid or gel covering directly onto the face. This allows the mixing and application of a variety of topical treatments to the skin being treated. In other instances, a facial mask may be created by saturating a cloth-like material with a particular topical treatment. This homogeneous treatment can then be applied to the face such that the topical treatments on the cloth-like material will contact the face.

Often times, facial masks are applied to the user's face, and then covered by a warm towel to heat and activate the mask solutions, and to improve absorption into the skin. These warm towels may serve to activate the solutions; however, the towels tend to cool quickly so that the mask returns to room temperature long before the facial treatment is over. Alternatively, it is often advantageous to provide a cooling facial mask. Currently, these cool facial masks are applied with a cool towel, which when applied to the person's skin, quickly warm up to ambient temperature. The use of ice, while appropriate in a trauma situation, is impractically cold for a relaxing facial treatment.

Unfortunately, currently available facial masks on cloth-like materials are homogeneous across the entire face. For instance, the same facial mask solution is applied to the cheeks and to the nose, despite the significant differences which can occur between the skin found on the nose and cheeks. Often, the skin on the nose tends to be more oily, and the skin on the cheeks tends to be more dry. Thus, some users with oily skin may choose a facial mask with a higher concentration of clay to absorb excess oil, whereas that same treatment has a detrimental effect on the already-dry cheek skin. Similarly, users that may be worried about facial wrinkles might choose a treatment that is hydrating and high in antioxidants and vitamins that are perceived to slow the process of aging, whereas that same treatment may compound the production of oils when applied to oily skin.

In light of the above, it would be advantageous to provide a facial mask that accommodates varying skin types over the same mask. It would also be advantageous to provide a treated non-woven or paper backed facial mask. It would also be advantageous to provide a heated or cooling mask which maintains its desired temperature for an extended period of time.

SUMMARY OF THE INVENTION

The temperature controlled facial mask with area-specific treatments of the present invention includes a substantially planar mask body which is formed with cut-outs for a person's eyes, nose, and mouth. On the front side of the mask body, the face mask may include a number of large and small area treatment zones in combination with asymmetrical treatment zones suitable for treatment of specific and localized skin conditions. The treatment zones are coated with skin treatments, such as compounds, lotions, gels, and the like as are known in the facial treatment, cosmetics, spa and medical industries. On the backside of the mask body, a self-heating or cooling substrate may be applied to provide temperature control to the face mask.

A system is also provided that includes an imaging device that feeds its output to a central computer system having an image analyzer, CPU, memory and Look Up Table, and face map for determining specific treatment requirements for the particular patient. An output from the central computer system is provided to a treatment deposition device which deposits its various treatments onto an intermediate membrane layer to generate a custom temperature controlled facial mask with area-specific treatments for that particular patient.

BRIEF DESCRIPTION OF THE DRAWINGS

The nature, objects, and advantages of the present invention will become more apparent to those skilled in the art after considering the following detailed description in connection with the accompanying drawings, in which like reference numerals designate like parts throughout, and wherein: FIG. 1 is a top plan view of the temperature controlled facial mask with area-specific treatments of the present invention showing a planar mask body having cut-outs for eyes, nose, and mouth, and showing a number of symmetrical treatment zones (shown in dashed lines);

DETAILED DESCRIPTION OF A PREFERRED EMBODIMENT

Figure 1:
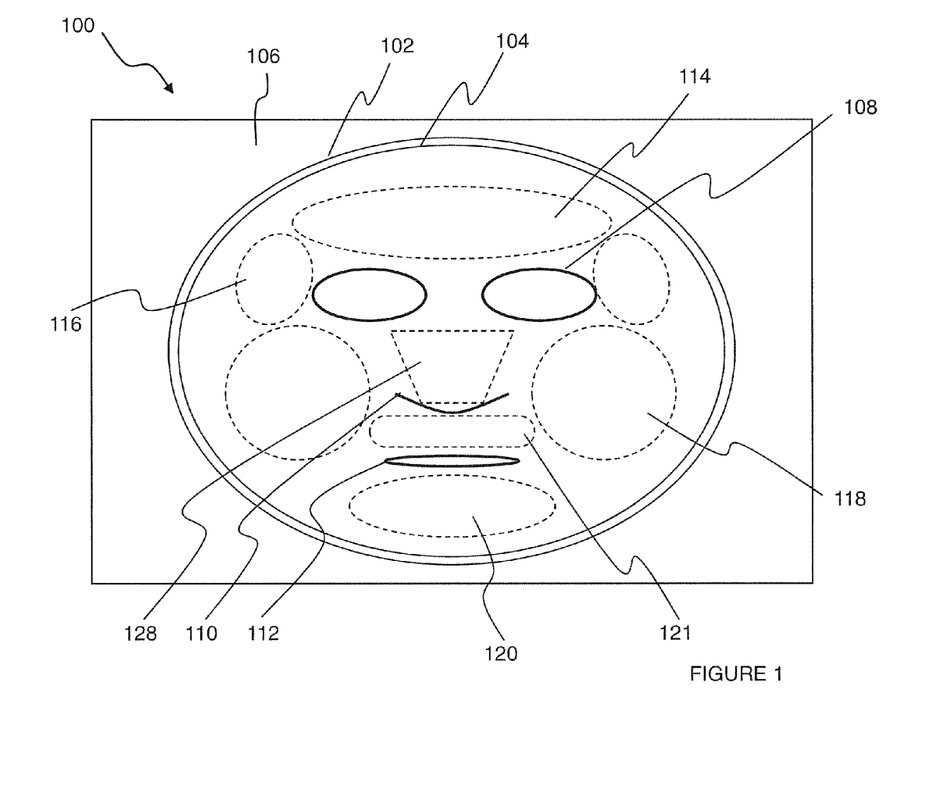
FIG. 1 is a top plan view of the temperature controlled facial mask with area-specific treatments of the present invention showing a planar mask body having cutouts for eyes, nose, and mouth, and showing a number of symmetrical treatment zones (shown in dashed lines)

Referring initially to FIG. 1, a top plan view of the temperature controlled facial mask with area-specific treatments of the present invention is shown and generally designated 100. A substantially planar mask body 102 is formed to have a treatment area 104 which extends, in most cases, to the perimeter of the mask 102. In some applications, however, it may be advantageous to limit the treatment area to less than the surface of the mask 102.

Mask 102 may be manufactured and supplied on a backing sheet 106 which, as will be described more fully below, may facilitate the manufacturing of the area-specific treatments on the mask 102. Mask 102 also formed with cut-outs for eyes 108, nose 110, and mouth 112. These facilitate the easy viewing, breathing and talking by the person wearing the mask during a facial treatment.

From FIG. 1, a number of symmetrical treatment zones, shown in dashed lines, can be seen. Specifically, mask 102 is formed with a forehead treatment zone 114, temple treatment zones 116, cheek treatment zones 118, chin treatment zone 120, upper lip treatment zone 121, and nose zone 128.

The various treatment zones as shown in FIG. 1 are merely exemplary of a preferred embodiment of the temperature controlled facial mask with area-specific treatments of the present invention. It is to be appreciated that these particular zones may be repositioned based on a particular patient's requirements, or the entire mask may have a consistent treatment across its entire surface.

Figure 2:
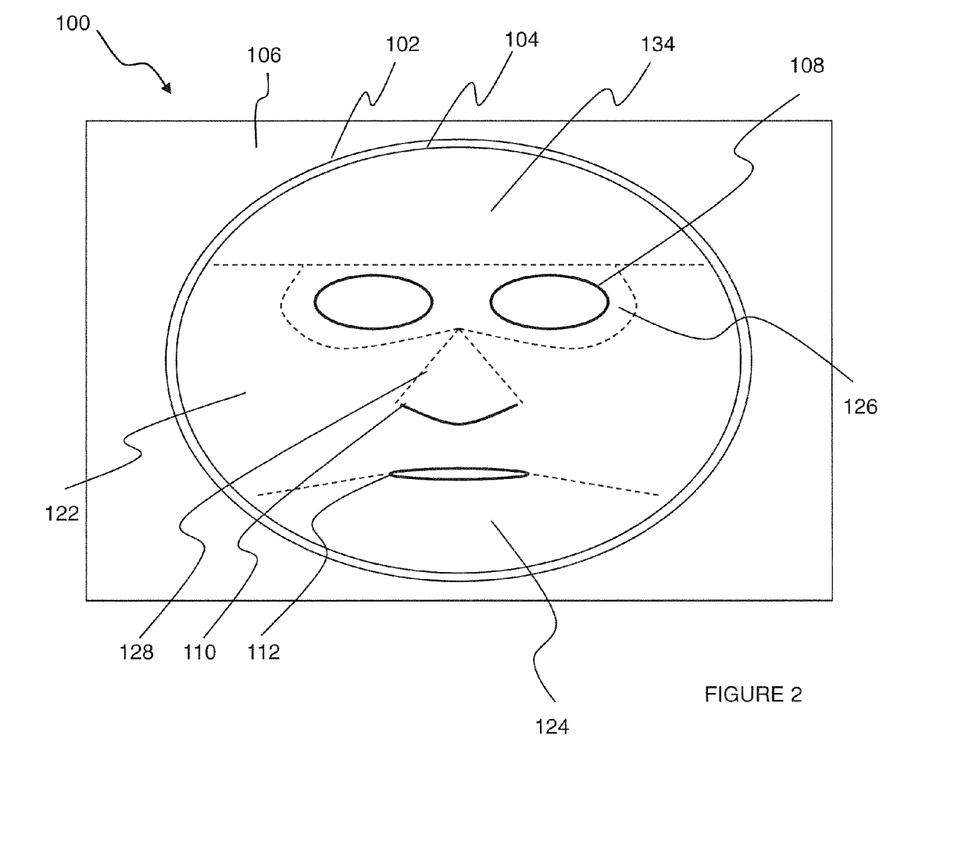
FIG. 2 is a top plan view of an alternative embodiment of the temperature controlled facial mask with area-specific treatments of the present invention showing a planar mask body having cut-outs for eyes, nose, and mouth, and showing a fewer number of symmetrical large-area treatment zones (shown in dashed lines)

FIG. 2 is a top plan view of an alternative embodiment of the temperature controlled facial mask with area-specific treatments 100 of the present invention. This embodiment shows the planar mask body 102 having cut-outs for eyes 108, nose 110, and mouth 112. This embodiment, however, includes a fewer number of symmetrical large-area treatment zones than those of FIG. 1. For instance, there is a temple and cheek zone 122, a lower facial zone 124, an eye mask zone 126, a nose zone 128 and abroad forehead zone 134.

Figure 3:
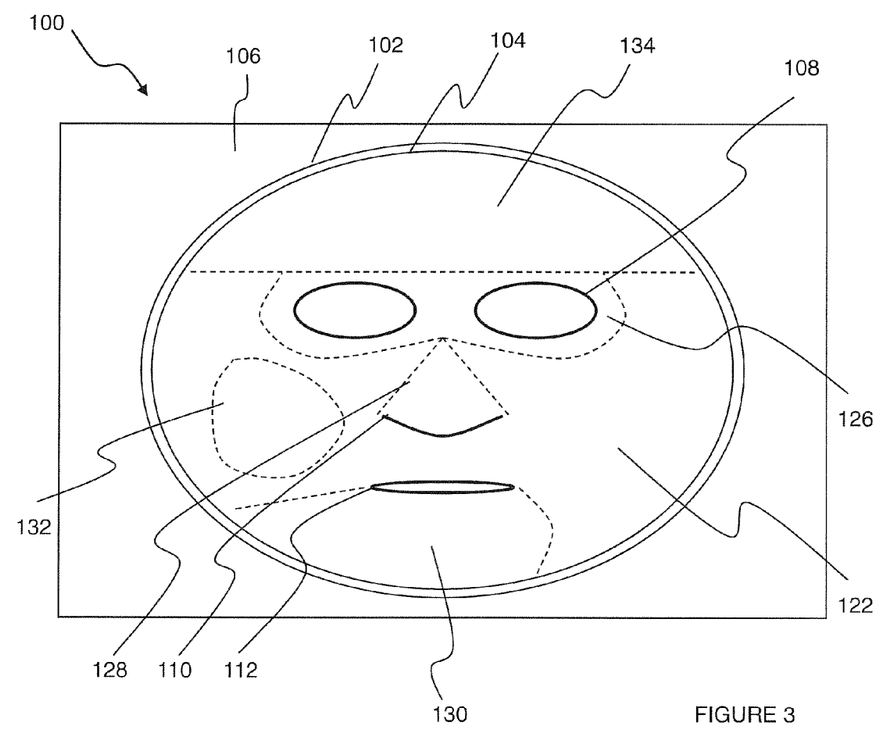
FIG. 3 is a top plan view of another alternative embodiment of the temperature controlled facial mask with area-specific treatments of the present invention showing a planar mask body having cut-outs for eyes, nose, and mouth, and showing a number of symmetrical large-area treatment zones in combination with asymmetrical treatment zones suitable for treatment of specific and localized skin conditions (shown in dashed lines)

Referring to FIG. 3, a top plan view of another alternative embodiment of the temperature controlled facial mask with area-specific treatments 100 of the present invention is shown. This embodiment includes a planar mask body 102 having cut-outs for eyes 108, nose 110, and mouth 112, and also includes a number of symmetrical large-area treatment zones in combination with asymmetrical treatment zones suitable for treatment of specific and localized skin conditions. More specifically, a broad forehead treatment zone 134, nose treatment zone 128, and a broad temple and cheek treatment zone 122 may be used to treat large-area conditions. In addition, mask 102 may include some localized treatment zones such as eye mask zone 126, asymmetrical chin zone 130, and cheek zone 132. In these instances, a highly specialized treatment mask 102 may be provided which treats general skin conditions with large-area treatment zones, yet provides for very localized treatment zones for specific skin treatments.

While the various figures disclosed herein have depicted a facial mask having an oval, whole-faced shape, it is to be appreciated that other shapes may be used without departing from the temperature controlled facial mask with area-specific treatments of the present invention. For instance, in some cases, it may be advantageous to provide a mask for only treating the areas around the eyes, and in that case, the entire mask might resemble the eye mask zone of FIG. 2. Alternatively, in certain treatment procedures, small masks may be made having unique shapes to contour match a particular body part, such as a neck or shoulder for area-specific treatments.

Figure 4:
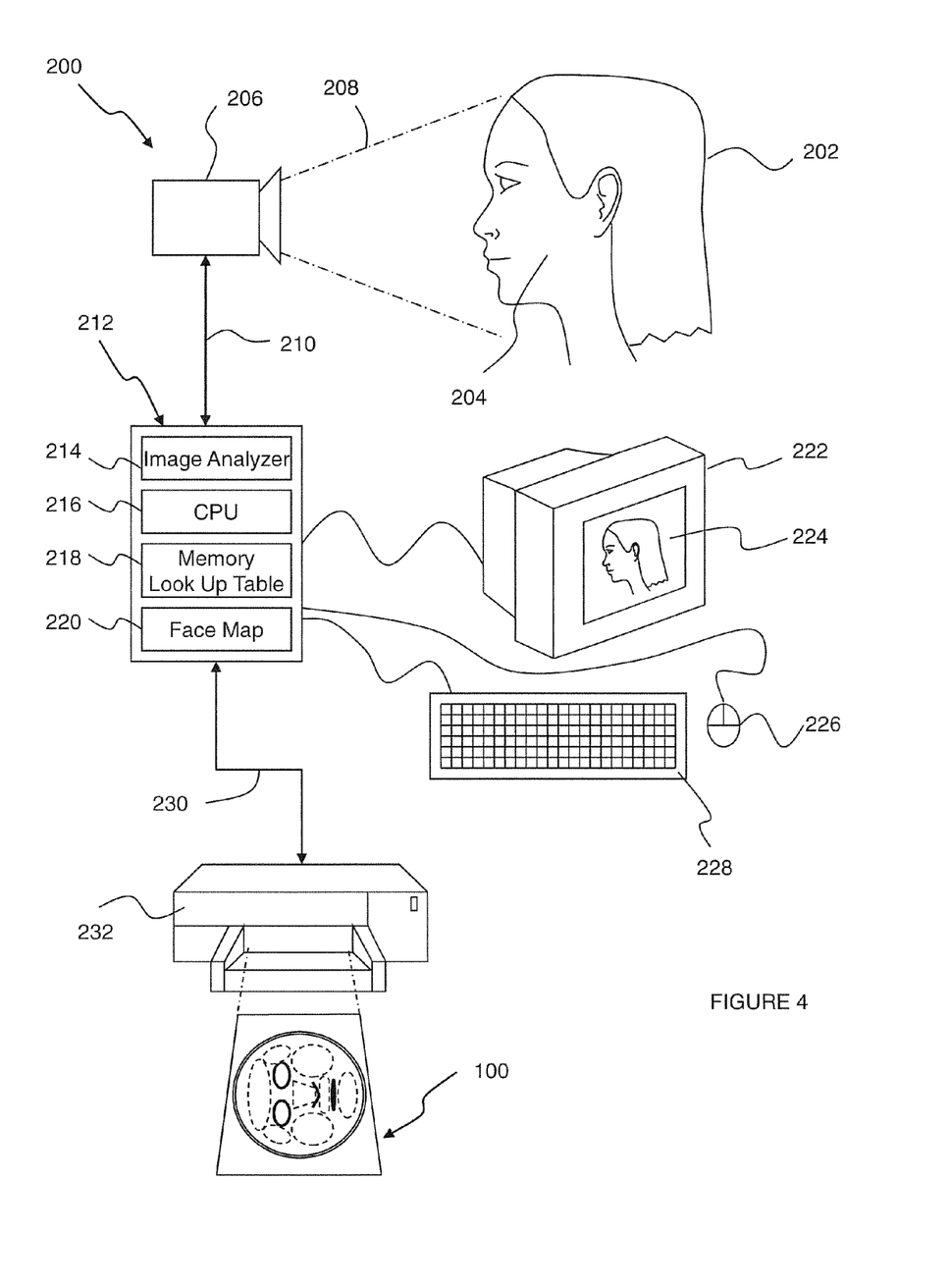
FIG. 4 is a system diagram of the system for creation of the temperature controlled facial mask with area-specific treatments of the present invention showing a patient being scanned by an imaging device which feeds its output to a central computer system having an image analyzer, CPU, memory and Look Up Table, and face map for determining specific treatment requirements; an output from the central computer system is provided to a treatment deposition device which deposits various treatments onto an intermediate membrane layer on top of a self-heating or cooling substrate to create a temperature controlled facial mask with area-specific treatments.

FIG. 4 provides a system diagram of the system for creation of the temperature controlled facial mask with area-specific treatments of the present invention, and is generally designated 200. System 200 includes a patient 202 with her face 204 positioned in the field of scan 208, and being scanned by an imaging device 206. This imaging device 206 is capable of sensing many characteristics from the patient's face 204. For instance, device 206 may sense infrared emissions from areas of increased heat, reflectivity sensing oiliness or dryness of the skin, and defects such as wrinkles and blemishes. These characteristics are merely exemplary a preferred embodiment, however, it is to be appreciated that such examples are not intended to limit the functionality of imaging device 206 as any imaging device known in the art is fully contemplated herein.

The imaging device 206 provides an output 210 which is in electrical communication to a central computer system 212 having an image analyzer 214, CPU 216, memory and Look-Up Table 218, and face map 220. In use, the output 210 from the imaging device 206 is passed through an image analyzer 214. The data from the image analyzer is manipulated by the CPU 216 and the analyzed data is then stored into memory and compared to Look-Up table 218. Based on the analysis of the patient's facial scan and comparison to data from the Look-Up table, a specific treatment protocol is determined and stored as a face map 220.

In circumstances where the scan reveals a portion of the patient's skin is oily, the look-up table 218 may identify an anti-oil treatment such as a natural mud. In circumstances where the scan reveals a portion of the patient's skin is dry, the look-up table 218 may identify a hydrating lotion to replenish the moisture in the skin.

A face map 220 may include very specific information regarding the patient's face. For instance, a patient having a combination of skin conditions, such as an oily nose, dry cheeks, and crow's feet wrinkles adjacent her eyes, would have a specific treatment protocol to address each of these issues. On the other hand, a patient having an overall oily skin condition, yet has no wrinkle issues, would have a completely different treatment protocol.

System 200 also includes a display 222 providing an operator with a screen 224 from which to view the patient 202. By utilizing the user interfaces, such as mouse 226 and keyboard 228, an operator may customize a treatment proto-col based on the face map, as well as the patient's preferences.

Utilizing this user interface, an operator may change, modify and store in memory a patient's treatment protocol. Such information may be stored in a database and identifiable using the patient's name or identification number. This is particularly advantageous when treating a patient on multiple occasions. In such an application, a patient could simply present him or herself at a treatment facility and, by providing his or her name or identification number, the precisely customized treatment protocol would be retrieved from the memory. Indeed, the entire patient's protocol history could be stored in memory 218, and retrievable on demand.

In circumstances where a chronic skin condition is being treated, it may be advantageous to maintain the same treatment protocol for a series of treatments. On the other hand, in some cases it might be advantageous to access the baseline protocol for the patient, and then make slight adjustments, such as for resolving skin conditions, or for seasonal weather changes.

The particular deposition pattern and contents may be determined by the analysis of a patient's facial skin conditions (or input from a user interface such as the computer keyboard 228 and mouse 226 and in turn, may compare this data to known treatment protocols contained in a look-up table 218. Based on the analysis, and comparison if made, a patient-specific heated face mask 100 may be created to provide the patient 202 with area-specific treatments. This is particularly useful in circumstances where, for instance, a patient's facial skin may be suffering from localized dryness, oiliness, wrinkles, blemishes, or the like. Using the temperature controlled facial mask with area-specific treatments 100, a patient 202 may obtain specific and repeatable treatment to problem areas.

A patient, once analyzed, can have the particular treatment protocol stored in the memory of the central computer system. This enables the patient to return to the treatment center over the course of time to receive the identical facial mask treatments, or the protocol may be retrieved and modified slightly based on success or failure of the treatment to optimize treatment of the patient's skin.

Once the particular treatment protocol is determined, an output 230 from the central computer system 212 is provided to a treatment deposition device 232. Treatment deposition device 232 receives the output 230 from computer system 212 and, in response, deposits various treatments onto a printable membrane, or a self-heating substrate, to create a temperature controlled facial mask with area-specific treatments 100.

While the application of various treatments has been described as being produced by treatment deposition device, it is to be appreciated that other deposition techniques may be implemented without departing from the present invention. For instance, lithographic and screen printing processes, rotogravure, inkjet, bubble jet, and laser printing techniques as are known in the art are fully contemplated herein.

Figure 5:
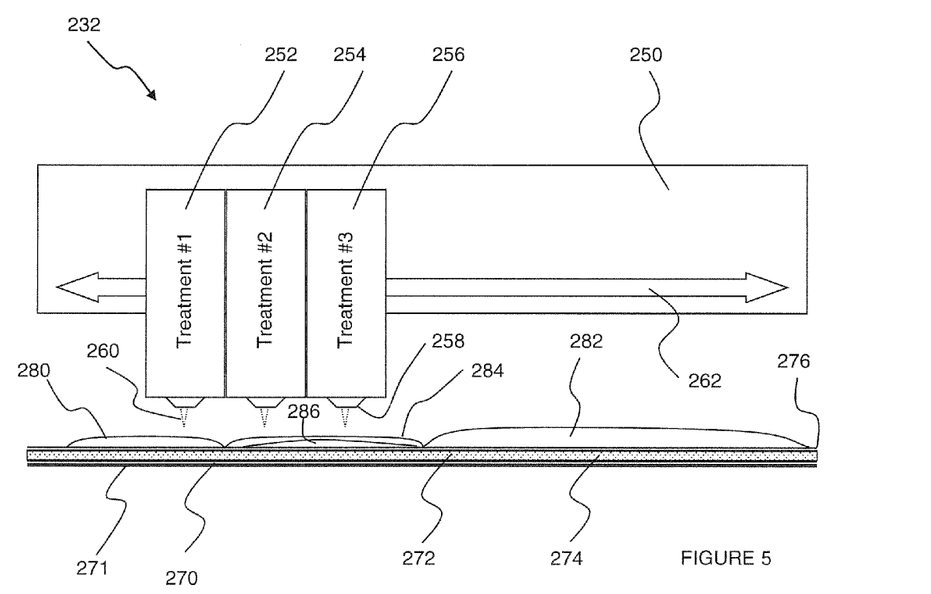
FIG. 5 is a detailed side view of the treatment deposition device which includes a number of treatment reservoirs that contain skin treatments (compounds, lotions, gels, and the like as are known in the facial treatment, cosmetics and spa industry), and through direction of the central computer system based on analysis of the patient's skin's needs, one or more of the treatments is deposited onto the printable membrane or self-heating substrate.

Referring now to FIG. 5, a detailed side view of the treatment deposition device 232 is shown and includes a translation slide, or track, 250. A number of treatment reservoirs 252, 254, and 256 that contain skin treatments (compounds, lotions, gels, and the like as are known in the facial treatment, cosmetics and spa industry). Reservoirs 252, 254, and 256 each have a nozzle 258 from which treatment materials are discharged as shown by dashed lines 260.

The reservoirs are positionable along track 250 in direction 262. Through direction of the central computer system 212 based on analysis of the patient's skin's needs, one or more of the treatments reservoirs 252, 254, and 256 is activated to discharge a portion of its contents onto the self-heating substrate or printable membrane as that membrane moves through treatment deposition device. More specifically, based upon instructions from computer 212, a number of different treatment regions may be created on the face mask. For instance, distinct treatment regions 280 and 282 may be formed on a non-woven, paper, rice paper, plastic or other membrane 276. Also, regions may overlap on membrane 276, such as treatments 286 covering 284, so that the patient's skin may receive the combined treatment benefits of more than one topical.

In the embodiment of the temperature controlled facial mask with area-specific treatments of the present invention shown in FIG. 5, a temperature controlling substrate is presented. A backing sheet 271, such as a polyethylene sheet, is adjacent a layer 270 of absorptive non-woven, cotton fabric, paper, or the like, is covered with a layer of synthetic fiber 272, commonly referred to as "fluff". An amount of reactive mineral 274 is interspersed or captured in the fluff layer 272. The particular amount of reactive mineral may be adjusted to achieve varying heating or cooling characteristics. Non-woven layer 276 is then positioned over layer 272. Alternatively, an amount of reactive mineral may be positioned on backing sheet 270 and sandwiched in place with an absorptive non-woven, with small amounts of the reactive mineral being sealed in place using a heat or ultra-sonic sealing technique known in the art. This method distributes the reactive mineral evenly across the surface of the backing sheet 270 thereby providing even heating or cooling across the surface of the facemask. Alternatively, a fine glue spray may be used to adhere the active mineral to the substrate and to prevent the migration of the active mineral during manufacturing, shipping, and use.

In use, a hydrating agent, such as water, is applied to layer 272 which by its characteristics allow the water to penetrate the layer exposing the active mineral 274 to moisture. This moisture creates a chemical reaction, either exothermic or endothermic, to provide the desired heating and/or cooling effect.

Hydration of the active mineral layer 272 may be accomplished from exposing the side of the panel 272 to water and by the natural characteristics of water migration through the layers; the entire layer will be hydrated. Also, manual palpitation of the layer can be used to increase the water flow throughout the layers.

Figure 6:
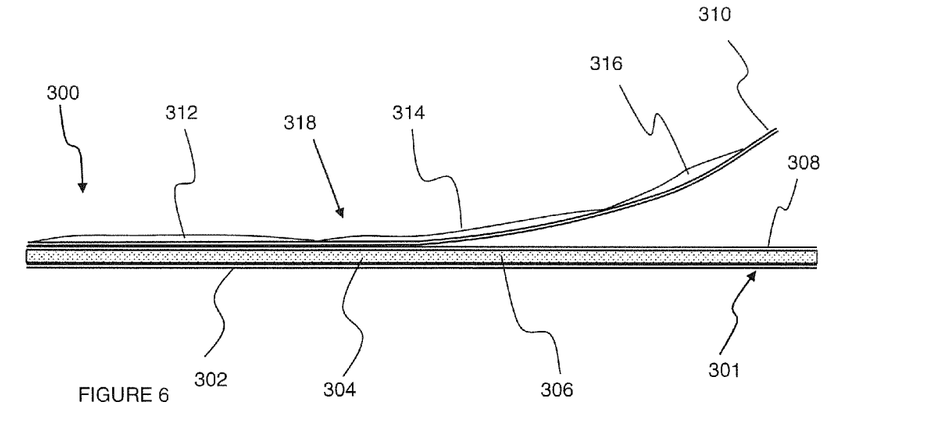
FIG. 6 is a side view of the temperature controlled facial mask with area-specific treatments of the present invention showing the configuration of skin treatments on a printable membrane which is attachable to a temperature regulated substrate for heating and/or cooling the skin treatments and adjacent skin.

Referring now to FIG. 6, a side view of an alternative embodiment of the temperature controlled facial mask with area-specific treatments of the present invention is shown and generally designated 300. Mask 300 includes a configuration of skin treatments on a non-woven (or the like) printable membrane 310. More specifically, membrane 310 has treatment regions 312, 314, and 316 that may contain different active topical compounds as is known in the art.

This printable membrane may, be created separately, and without any additional heating or cooling apparatus. In such circumstances, the output 230 from computer system 212 would direct the treatment deposition device 232 to deposit various treatment materials into the treatment regions 312, 314, and 316 on membrane 310. Once completed, the treated side 318 of membrane 310 may be applied directly to the patient's face or other body part. If desired, separate heating or cooling may be applied over the printable membrane 310. Since membrane 310 is water permeable, a moist heated or cooled towel would activate the topical treatment materials, as well as provide a pleasant spa treatment to the patient.

In some applications, mask 300 may be formed by depositing the treatments 312, 314, and 316 on membrane 310. Membrane 310 may then be attached to a temperature regulated substrate 301 for heating and/or cooling the skin treatments and adjacent skin. Temperature regulated substrate 301 includes a backing sheet 302, such as non-woven, perforated tissue paper or perforated polyethylene, covered with synthetic non-woven materials, such as fluff layer 304. Fluff layer 304 contains an active mineral 306, and is covered by a layer of absorbent non-woven material 308. The absorbent non-woven material 308 allows water to pass through it, thereby activating the active mineral and providing the desired heating or cooling effect.

A facial mask having a heated substrate is discussed here, with the cooling substrate discussed below. The self-heating substrate of the present invention may include a compound of super absorbent polymer (SAP) with magnesium and iron such that with the introduction of water and necessary salts, an exothermic chemical reaction occurs and produces heat. The salt may be included in the reactive mineral compound, or it may be added to the water used to active the reactive mineral. The incorporation of a super absorbent polymer within the compound provides a number of unusual and unexpected key advantages. For instance, the presence of the super absorbent polymer buffers the reaction so that the reaction is less violent than the reaction would be without the polymer additive. Also, because the super absorbent polymer attracts water molecules which can then be drawn out for reaction with the active mineral compound, the chemical reaction lasts far longer than a compound without the polymer.

The present invention, in a preferred embodiment, includes a generally rectangular-shaped intermediate self-heating or cooling substrate made from various layers. Specifically, a base sheet of polyethylene film is provided and establishes a base from which the remaining layers are positioned. A layer of non-woven fabric is positioned over the polyethylene film layer and followed with a layer of fluff, and then a layer of active mineral compound, such as magnesium-iron powder, for instance for a heating substrate, is sprinkled over a fluff layer, and covered with a layer of either tissue paper, or non-woven. In addition, the layer of polyethylene which can be added to eliminate evaporative cooling from the backside of the substrate, thereby prolonging the heating reaction and providing a longer treatment period.

The spun layer, or absorptive non-woven, is intended to allow water to pass through the material. In use, the temperature changing substrate of the present invention is hydrated, such as by placing the substrate in a tray and adding water (and salt if necessary) into the tray such that the water passes through the spun layer to activate the active mineral layer in the fluff. In response to the hydration, the active mineral provides heating (or cooling) in an amount determined by the composition of the active mineral, and can range from a few minutes to over an hour.

It should be appreciated that other active mineral compounds which produce heating and cooling reactions when activated may be used in the present invention without departing from the spirit of the invention. The active minerals embodied in the present invention include minerals which exhibit exothermic reactions, such as those using reduction reactions of calcium oxide (e.g. quick-lime) and magnesium-iron. These reactions are typically initiated using water, or salt and water, and continue for some time. The active mineral compound may be further accompanied by one of several types of super-absorbent polymers ("SAP") known on the market. The combination of the exothermic mineral reaction, coupled with the water-absorption characteristics of the SAP, provides for a prolonged exothermic or endothermic chemical reaction which provides for heat periods ranging up to and exceeding an hour.

The present invention is useful as a water-activated source for heating or cooling. It is fully contemplated that other types of products may be made using the same invention as the temperature controlled facial mask with area-specific treatments described herein. The incorporation of any specific endothermic or exothermic active mineral compound, the SAP, and the layers of materials to create the temperature changing substrate may be utilized for other applications without departing from the spirit of the present invention.

It is to be appreciated that other heating techniques which are not self-heating may be utilized with the temperature controlled facial mask with area-specific treatments of the present invention. Further, heated towels may be used to activate the treatments on the face mask and provide a heated treatment, or cooled towels may be used to activate the treatments on the face mask and provide a cooled treatment.

In addition to heat producing, or exothermic, reactions, endothermic reactions are also advantageous in the temperature controlled facial mask with area-specific treatments of the present invention in order to provide an extended cooling effect. Given the proximity to a person's skin and the ability to easily begin the reaction, endothermic reactions where water is one component are particularly advantageous. For instance, the mixing water and ammonium nitrate, or water with potassium chloride, can have a cooling effect. Also, the dissolving of ammonium chloride in water creates an endothermic reaction to provide the desired cooling effect.

In other embodiments of the temperature controlled facial mask with area-specific treatments of the present invention, endothermic compounds/reactions involving chemical as both components can be used. For instance, the reaction of barium hydroxide octahydrate crystals with dry ammonium chloride provide a cooling effect. Also, the reaction of thionyl chloride ($SOCl_2$) with cobalt (II) sulfate heptahydrate, as well as reacting ethanoic acid with sodium carbonate, can provide a desired cooling effect.

In another preferred embodiment, cooling effects can be provided by utilizing mechanical or non-chemical Heat Pump or Heat Transfer Technology. This approach is very effective, but must be sized on a micro or nano-scale for cosmetic purposes. Basically, this approach includes the evaporating of liquid water into a void or hollow structure using an adsorbent in a vacuum. The endothermic reaction is best realized by using the evaporation of water into a vacuum chamber containing an adsorbent material encapsulated within. There is an adsorbent material in the vacuum chamber that adsorbs the water and contains it. This is the most powerful type of self cooling. The cooling properties of endothermic reactions are significantly less than the cooling provided by controlled evaporation. The theory of controlled evaporation is that the evaporation of 10 ml of water can cool 330 ml of water by 18 degrees C.—or almost 65 degrees F. in a completely safe way, no chemical reaction is involved, simply the mechanical heat transfer.

In a preferred embodiment of the temperature controlled facial mask with area-specific treatments of the present invention, the evaporative cooling technology will include micro-encapsulation to form tiny vacuum chambers of adsorbent materials, such as zeolites or other nano-structure vehicles. Additionally, it would be advantageous to vacuum the zeolite particles, which are natural adsorbents themselves and also act as the container, and micro encapsulate them with a water soluble coating (under vacuum). This coating would act as a membrane that slowly dissolves and passes water within. When the tiny globe of the zeolite structure is evacuated, the potential is that the water would be drawn into the vacuum chamber of the interior structure of the zeolite, causing cooling by evaporation and adsorption.

It is to be appreciated that the various chemical or mechanical reaction-based exothermic and endothermic reactions are merely exemplary of a preferred embodiment of the temperature controlled facial mask with area-specific treatments of the present invention. The specific suitability of one reaction type over another would be determined by the specific application area, the facial mask compounds being used, and the magnitude and duration of the intended heating or cooling desired.

In certain applications, it would be advantageous to provide a temperature controlled facial mask with area-specific treatments of the present invention that has portions of the mask which heat during the treatment, and other portions of the mask which simultaneously cool during the treatment. Accordingly, it is fully contemplated herein that there may be regions of the mask having an active mineral or chemical compound which are exothermic in some regions, and endothermic in other regions. Also, it may be advantageous to provide regions with neither heating nor cooling effects, and in that case, such regions would be devoid of either heating or cooling effects.

Figure 7:
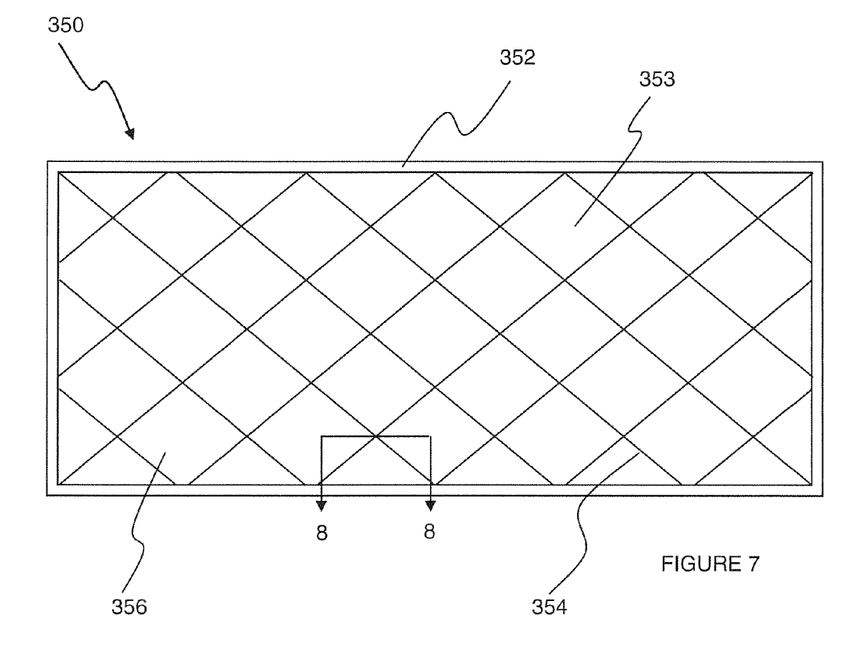
FIG. 7 is top plan view of an alternative embodiment of the temperature controlled facial mask with area-specific treatments of the present invention that includes a substrate that is formed to have multiple pouches which can contain an active mineral, such as for cooling or heating.
Figure 8:
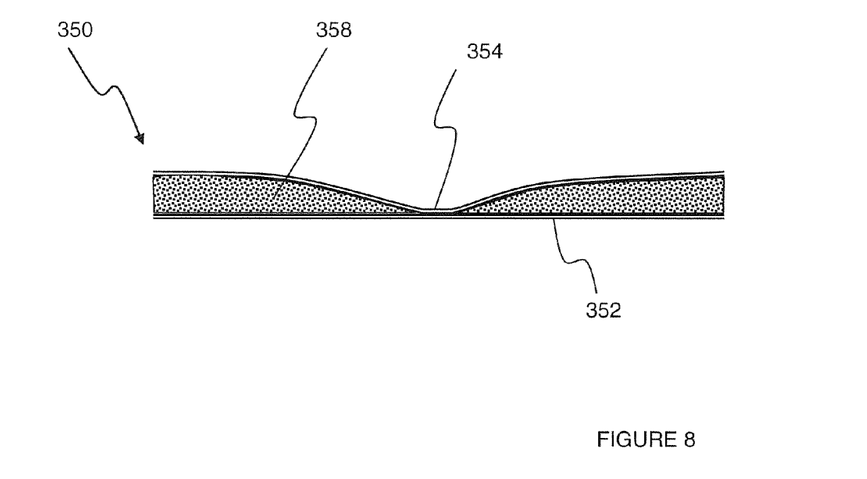
FIG. 8 is a cross-sectional drawing of the alternative embodiment of the temperature controlled facial mask with area-specific treatments of the present invention FIG. 7 taken along line 8-8, and depicts the seal between the backing panel and the upper panel with a volume of active mineral captured within each pouch.

FIG. 7 is alternative embodiment of the temperature controlled facial mask with area-specific treatments of the present invention that includes a substrate that is formed to have multiple pouches. More specifically, substrate 350 includes a backing panel 352 such as polyethylene or an absorptive non-woven. An upper panel 353, such as an absorptive non-woven, is positioned over panel 352 and a plurality of seals 354 are made to form a number of pouches 356. Each pouch 356 contains an active mineral, such as for cooling or heating, or may be empty to provide neither cooling or heating. FIG. 8 is a cross-sectional drawing of FIG. 7 taken along line 8-8, and depicts the seal between the backing panel 352 and the upper panel 353. Seal 354 may be made by a sonic seal as is known in the art, or by other traditional sealing techniques, such as an radio frequency (RF), adhesive (not shown this Figure), a heat seal, or the like.

Within each pouch 356, a volume of active mineral 358 is provided. In some instances, this active mineral 358 is accompanied by a volume of SAP which, when activated by water, will absorb a portion of the water and provide a pro-longed reaction. Activation of the temperature controlled facial mask with area-specific treatments of the present invention includes the addition of water, or water and salt, that initiates the chemical reaction. Water may pass through panels 352 and/or 353 to reach the active mineral.

Figure 9:
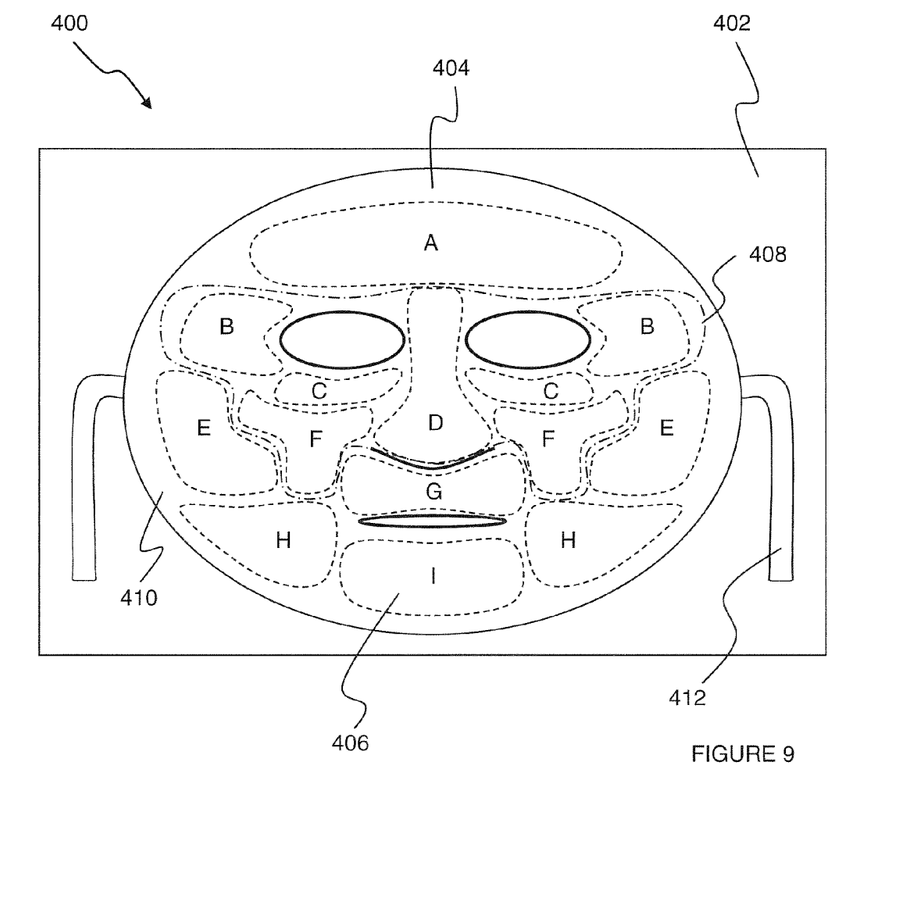
FIG. 9 is a top plan view of another alternative embodiment of the temperature controlled facial mask with area-specific treatments of the 5 present invention showing a planar mask body having cut-outs for eyes, nose, and mouth, and showing a number of symmetrical large and small area treatment zones.

Referring now to FIG. 9, an alternative embodiment of the temperature controlled facial mask with area-specific treatments of the present invention is shown and generally designated 400. Mask 400 includes a backing sheet 402 having a treatment area 404. Treatment area 404 is formed to have a number of very area-specific treatment zones 406. As shown in this Figure, zones A through I are shown as exemplary of a preferred embodiment. It is to be appreciated that these zones, while having a particularly advantageous configuration for facial treatments, are in no way limiting on the invention disclosed herein. In fact, the temperature controlled facial mask with area-specific treatments of the present invention may be made with any number of treatment zones, and any combination of heating, cooling or ambient (no heating or cooling) zones.

In some instances, it may be advantageous to provide certain portions of the temperature controlled facial mask with cooling properties, such as the area designated by dashed lines 408 around the eyes and cheeks. This would be particularly advantageous to treat Rosacea. Also, it may be advantageous to provide other portions of the temperature controlled facial mask with heating properties. Thus, in a single application, there may be portions of a mask which are cooled, and portions of the mask that are heated.

If desired, a pair of straps 410 may be formed from either backing sheet 402, or another layer of the mask of the present invention. The straps 410 may be used to tie the mask 400 onto the wearer's face to apply pressure to the mask and increase the contact area on the face.

The temperature controlled facial mask with area-specific treatments of the present invention is contemplated in several different facial mask approaches. First, a temperature controlled facial mask with area-specific treatments may be created by manually applying various treatments to the surface of a generic blank mask, and then applying that mask to a patient. Alternatively, an assortment of pre-treated masks may be created with treatment protocols which would tend to address most patients' skin issues, based on an accumulation of information and typical patient requirements. Alternatively, a temperature controlled facial mask with area-specific treatments of the present invention which would be electronically selected by a user and arranged on the mask based on the patient's skin characteristics and needs. Yet another alternative device would be a system that would select and arrange area-specific treatments by an automated skin analysis scanner in combination with a treatment deposition device.

The look-up table as described herein is intended to associate certain types of skin types and conditions with certain treatment protocols. For instance, the table below provides an exemplary look-up table and how it may be used in a preferred embodiment to determine the specific treatments to be applied to a patient.

| Skin Type | Condition | Treatment Protocol |
|---|---|---|
| Dry | | A |
| Oily | | B |
| | Acne | 1 |
| | Rosacea | 2 |
| | Scarring | 3 |
| | Wrinkles | 4 |

Based on the exemplary look-up table above, a patient having dry skin would be treated with protocol 'A', and protocol 'B' if his skin is oily. In circumstances where the patient's skin is both oily, and he suffers from rosacea and wrinkles, that patient protocol would include 'B' '2' and '4'. It is to be appreciated that the table above is simplified as an example of the detection of skin conditions, and the selection process for various protocols. Further, while the particular protocol may be identified by a simple alphanumeric character, it nevertheless may represent a very complex compound of various organic, pharmaceutical and therapeutic agents.

In a preferred embodiment, some Typical Skin conditions and some active topical treatments can include:

| | |
|---|---|
| Acne | Salicylic acid, benzoyl peroxide, retinoids, topical acne antibiotics, azelaic acid |
| Oily Skin | Hot water (to dissolve oils) with lightly medicated soaps, clays or muds, sebaceous secretion inhibitors, Tea Tree oil |
| Dry Skin | Moisturizers, skin barriers builders to seal in moisture |
| Rosacea | Cooling pressure (to reduce redness and restrict blood vessels), topical azaleic acid, metronidazole, tretinoin, or sulfur preparations |
| Wrinkles | Muscle relaxers, collagen, chemical peels, |
| Hyper pigmentation | Skin lighteners, vitamin C |

While there have been shown what are presently considered to be preferred embodiments of the present invention, it will be apparent to those skilled in the art that various changes and modifications can be made herein without departing from the scope and spirit of the invention.

What is claimed is:

1. A method for making an apparatus for individualized area-specific skin treatments for a subject, wherein the apparatus is adapted to be placed on the skin of the subject, comprising the steps of: (a) scanning a plurality of area-specific skin treatment zones of the subject with an imaging device to generate an output; (b) communicating the output to an image analyzer to produce a data set; (c) using the data set to determine an individualized treatment protocol; (d) treating a membrane by communicating the individualized treatment protocol to a treatment deposition device adapted to receive the individualized treatment protocol and deposit the individualized area-specific skin treatments onto the membrane; (e) providing a substantially planar multiple layer apparatus comprising: a water impermeable backing panel; a water permeable upper panel; and a temperature-changing substrate that when contacted with an activator produces an exothermic or endothermic chemical reaction; and (f) attaching the membrane to the multiple layer apparatus.

2. The method according to claim 1, wherein the apparatus for individualized area-specific skin treatments for a subject is a facial mask.

3. The method according to claim 2, wherein the area-specific skin treatment zones further comprise a forehead treatment zone, two temple treatment zones, two cheek treatment zones, a chin treatment zone, an upper lip treatment zone, and a nose treatment zone.

4. The method according to claim 2, wherein during step (a) the imaging device senses infrared emissions, reflectivity or skin defects.

5. The method according to claim 2, wherein the deposited skin treatments include an active topical selected from the group consisting of: salicylic acid, benzoyl peroxide, retinoids, topical acne antibiotics, azelaic acid, hot water with lightly medicated soaps, clay, mud, sebaceous secretion inhibitors, tea tree oil, moisturizers, skin barrier builders, topical azaleic acid, metronidazole, tretinoin, sulfur preparations, muscle relaxers, collagen, chemical peels, skin lighteners and vitamin C.

6. The method according to claim 2, wherein the treatment deposition device utilizes deposition techniques selected from the group consisting of lithographic printing processes, screen printing processes, rotogravure printing processes, inkjet printing processes, bubble jet printing processes, and laser printing processes.

7. The method according to claim 2, wherein the membrane is made from a non-woven material.

8. The method according to claim 7, wherein the non-woven material is selected from the group consisting of paper or plastic.

* * * * *